US012742147B2

(12) United States Patent
Vainikka et al.

(10) Patent No.: US 12,742,147 B2
(45) Date of Patent: Sep. 22, 2026

(54) METHODS AND SYSTEMS FOR GROWING MICROBIAL MASS

(71) Applicant: Solar Foods Oyj, Vantaa (FI)

(72) Inventors: Pasi Vainikka, Lappeenranta (FI); Juha-Pekka Pitkänen, Lappeenranta (FI)

(73) Assignee: Solar Foods Oyj, Vantaa (FI)

( * ) Notice: Subject to any disclaimer, the term of this patent is extended or adjusted under 35 U.S.C. 154(b) by 357 days.

(21) Appl. No.: 18/550,815

(22) PCT Filed: Feb. 18, 2022

(86) PCT No.: PCT/FI2022/050105
§ 371 (c)(1),
(2) Date: Sep. 15, 2023

(87) PCT Pub. No.: WO2022/207963
PCT Pub. Date: Oct. 6, 2022

(65) Prior Publication Data

US 2024/0218315 A1 Jul. 4, 2024

(30) Foreign Application Priority Data

Mar. 31, 2021 (FI) ...................................... 20215382

(51) Int. Cl.

| | |
|---|---|
| ***C12N 1/20*** | (2026.01) |
| ***C12M 1/00*** | (2006.01) |
| ***C12M 1/06*** | (2006.01) |
| ***C12M 1/34*** | (2006.01) |
| ***C12M 3/04*** | (2006.01) |

(52) U.S. Cl.
CPC ............... *C12N 1/20* (2013.01); *C12M 23/58* (2013.01); *C12M 27/02* (2013.01); *C12M 27/10* (2013.01); *C12M 41/12* (2013.01); *C12M 41/26* (2013.01)

(58) Field of Classification Search
CPC ......... C12N 1/20; C12M 23/58; C12M 27/02; C12M 27/10; C12M 41/12; C12M 41/26; C12M 45/00; C12M 35/08; Y02E 50/30; C25B 1/04; C25B 15/081; C12R 2001/01
See application file for complete search history.

(56) References Cited

U.S. PATENT DOCUMENTS

| | | | |
|---|---|---|---|
| 4,041,182 | A | 8/1977 | Erickson et al. |
| 7,387,733 | B2 | 6/2008 | Baskis et al. |
| 9,206,451 | B2 | 12/2015 | Sefton |
| 2011/0027827 | A1 | 2/2011 | Chi et al. |
| 2017/0218404 | A1 | 8/2017 | Simpson et al. |

FOREIGN PATENT DOCUMENTS

| | | | |
|---|---|---|---|
| CN | 101405388 | A | 4/2009 |
| CN | 103958687 | A | 7/2014 |
| CN | 104550186 | A | 4/2015 |
| CN | 106701587 | A | 5/2017 |
| CN | 110678539 | A | 1/2020 |
| EP | 3816293 | A1 | 5/2021 |
| GB | 2029392 | A | 3/1980 |
| WO | 2017165244 | A1 | 9/2017 |
| WO | 2018144965 | A1 | 8/2018 |

OTHER PUBLICATIONS

Sillman et al., Global Food Security, vol. 22, 2019, pp. 25-32, ISSN 2211-9124, doi.org/10.1016/j.gfs.2019.09.007. (Year: 2019).*
Liu et al., Waste Management, vol. 34, Issue 9, 2014, pp. 1619-1626, ISSN 0956-053X, doi.org/10.1016/j.wasman.2014.05.027. (Year: 2014).*
Alvarado et al., "Food in space from hydrogen-oxidizing bacteria", Acta Astronautica, vol. 180, Dec. 13, 2020, XP086471331, ISSN: 0094-5765, DOI: 10.1016/J.ACTAASTRO.2020.12.009, 6 pages.
Clauwaert et al., "Nitrogen cycling in Bioregenerative Life Support Systems: Challenges for waste refinery and food production processes", Progress in Aerospace Sciences, vol. 91, May 4, 2017, XP085065961, ISSN: 0376-0421, DOI: 10.1016/J.PAEROSCI.2017.04.002, 12 pages.
Finnish Patent and Registration Office, Search Report, Application No. 20215382, Mailed Jul. 12, 2021, 3 pages.
Foster et al., "Engineering requirements for culturing of Hydrogenomonas Bacteria", SAE Technical Papers, 1967, Available on the Internet https://ntrs.nasa.gov>api>citations>downlaod, 8 pages.
European Patent Office, International Search Report and Written Opinion, Application No. PCT/FI2022/050105, Mailed Jun. 22, 2022, 18 pages.

(Continued)

*Primary Examiner* — Kade Ariani
(74) *Attorney, Agent, or Firm* — Espatent Oy

(57) ABSTRACT

A method of growing a microbial mass includes collecting biowaste from an organism, the biowaste comprising a first amount of water and a first amount of solid-phase; receiving the collected biowaste in a first reactor; treating the collected biowaste in the first reactor using a first set of operating parameters for a first period of time to dissolve at least a part of solid-phase inorganic nutrients into the first amount of water to form a growth media; washing the formed growth media, wherein said washing includes sterilization, separation and cleaning steps; providing the formed growth media to a second reactor including an inoculum of microbial mass; collecting carbon dioxide locally from an atmosphere; collecting a second amount of water present in the atmosphere and splitting the collected second amount of water into oxygen and hydrogen gas; providing the collected carbon dioxide and the split oxygen and hydrogen gas to the second reactor; growing a microbial mass in the second reactor under a second set of operating parameters; and harvesting the grown microbial mass from the second reactor to produce food for consumption by the organism.
Reference is made to the Identification of the Microorganism, with the identification reference given by the Depositor SoF1, having the Accession number given by the INTERNATIONAL DEPOSITORY AUTHORITY, VTT E-193585, received on Jun. 11, 2019.

16 Claims, 2 Drawing Sheets

(56) References Cited

OTHER PUBLICATIONS

Steinberg et al., "Convergent Microbial Community Formation in Replicate Anaerobic Reactors Inoculated from Different Sources and Treating Ersatz Crew Waste", Life, vol. 11, No. 1374, 11121374, Dec. 10, 2021, XP055916273, DOI: 10.3390/1ife11121374, 20 pages.
Steinberg et al., "Coupling of anaerobic waste treatment to produce protein- and lipid-rich bacterial biomass", Life Sciences in Space Research, vol. 15, Nov. 1, 2017, XP055916264, ISSN: 2214-5524, DOI: 10.1016/j.lssr.2017.07.006, 12 pages.
Yang et al., "Microbial protein production from CO2, H2, and recycled nitrogen: Focusing on ammonia toxicity and nitrogen sources", Journal of Cleaner Production, 2021 vol. 291, Available online Jan. 11, 2021, 9 pages.
Yu et al: "Carbon dioxide fixation by a hydrogen-oxidizing bacterium: Biomass yie1d, reversa1 respiratory quotient, stoichiometric equations and bioenergetics", Biochemical Engineering Journal, vol. 152, 107369, Sep. 9, 2019, XP085871573, ISSN: 1369-703X, DOI: 10.1016/J.BEJ.2019.107369, 10 pages.
Yu J. et al: "The energy efficiency of carbon dioxide fixation by a hydrogen-oxidizing bacterium.", International Journal of Hydrogen Energy, vol. 38, No. 21, May 31, 2013, XP028577206, ISSN: 0360-3199, DOI: 10.1016/J.IJHYDENE.2013.04.153, 8 pages.
Spitzer, R. Y. et al. Using hydrothermal carbonization for sustainable treatment and reuse of human excreta. In: Journal of Cleaner Production 205 (2018): 955-963. https://www.sciencedirect.com/science/article/abs/pii/S095965261832849X.
Liu, Chong, et al. Ambient nitrogen reduction cycle using a hybrid inorganic-biological system. In: Proceedings of the National Academy of Sciences, vol. 114, No. 25, Jun. 20, 2017. pp. 6450-6455. www.pnas.org/cgi/doi/10.1073/pnas.1706371114.
Matassa, Silvio et al. Resource recovery from used water: The manufacturing abilities of hydrogen-oxidizing bacteria. In: Water Research 68 (2015), pp. 467-478. Available online at www.sciencedirect.com.

* cited by examiner

METHODS AND SYSTEMS FOR GROWING MICROBIAL MASS

TECHNICAL FIELD

The present disclosure relates generally to growing microorganisms in closed-cycle systems for circulating nutrients; and more specifically to methods and systems for growing microbial mass. The present disclosure also relates to processes for growing microbial mass in non-gravitational field conditions.

BACKGROUND

Microorganisms have found use in various applications, ranging from medicine, food industry, biowaste management and the like. In this regard, microorganisms are typically grown in bioreactors under optimally balanced environmental conditions to produce microbial biomass for aforesaid applications, such as nutraceuticals, food and/or food ingredients, or bioremediation means. The optimally balanced environmental conditions include balanced amount of nutrients, gases, heat, pH and pressure. Recently, microorganisms have been employed in closed-cycle systems, such as space stations, for biowaste management as well as nutrient circulation with such systems. Notably, such use of microorganisms has been limited to only production of manure or fertilizers from the biological waste (or biowaste) for growing plants and for reducing the total landfill due to the disposal of the biowaste.

Conventionally, techniques for biowaste management utilize growing microbial mass, under controlled parameters in a growth chamber, by selecting suitable microorganism(s). Moreover, the conventional techniques for growing microbial mass in closed-cycle systems employ microorganisms to grow on biowaste by utilizing the nutrients therefrom. In an example, the conventional systems adopt continuous culturing techniques for microbial biomass production by utilizing hydrogen gas produced by electrolysis of water in closed-cycle system. The microorganisms used for such purpose may belong to a wide spectrum of genus, preferably, those that utilize carbon dioxide, urea and water to produce nutrients that may be used as food. However, the problem with the conventional systems is that they fail to utilize variety of biowastes, such as feces for example, as input for the system. Moreover, the biowastes contain urea, toxins, and other pathogenic bacteria and microorganisms toxic to growth media and humans, therefore requiring disposal of biowaste resulting in landfills and environmental pollution.

Recently, techniques have been introduced to recover inorganic material from the biowaste. A common method is to combust the biowaste to recover inorganic material, i.e. ashing of the inorganic material. However, such techniques also fail to completely recover inorganic material, such as nitrogen, iron, calcium, phosphorus, manganese, as during oxidization process at high temperatures inorganic materials lose their characteristics, for example elemental nitrogen is lost to nitrogen gas at high temperatures. Moreover, ash-forming elements form glass-like inactive silicates that cannot be recycled back as nutrients.

Therefore, in light of the foregoing discussion, there exists a need to overcome drawbacks associated with conventional techniques for growing microbial mass and achieving efficient nutrient retrieval and circulation.

SUMMARY

The present disclosure seeks to provide a method for growing microbial mass. The present disclosure also seeks to provide a system for growing microbial mass. Furthermore, the present disclosure seeks to provide a process for growing microbial mass in non-gravitational field conditions. The present disclosure seeks to provide a solution to the existing problem of efficiently converting biological waste into human edible material in a closed-cycle system. An aim of the present disclosure is to provide a solution that overcomes at least partially the problems encountered in prior art, and provides an efficient and robust technique for growing microbial mass, and consequently resulting in an effective and environmentally-safe nutrient circulation.

In an aspect, an embodiment of the present disclosure provides a method of growing a microbial mass, the method comprising collecting biowaste from an organism, the biowaste comprising a first amount of water and a first amount of solid-phase;

receiving the collected biowaste in a first reactor;

treating the collected biowaste in the first reactor using a first set of operating parameters for a first period of time to dissolve at least a part of solid-phase inorganic nutrients into the first amount of water to form a growth media;

washing the formed growth media, wherein said washing includes sterilization, separation and cleaning steps;

providing the formed growth media to a second reactor comprising an inoculum of microbial mass;

collecting carbon dioxide locally from an atmosphere;

collecting a second amount of water present in the atmosphere and splitting the collected second amount of water into oxygen and hydrogen gas;

providing the collected carbon dioxide and the split oxygen and hydrogen gas to the second reactor;

growing a microbial mass in the second reactor under a second set of operating parameters; and harvesting the grown microbial mass from the second reactor to produce food for consumption by the organism.

In another aspect, an embodiment of the present disclosure provides a system for growing microbial mass, the system comprising a first stage configured to collect biowaste from an organism, the biowaste comprising a first amount of water and a first amount of solid-phase, wherein the first stage is a collector unit;

a first reactor connected to the first stage to receive the collected biowaste from the first stage via an inlet, treat the received biowaste therein to form a growth media, and wash the formed growth media, wherein said washing includes sterilization, separation and cleaning, and wherein for treating the biowaste the first reactor comprising a temperature controller for maintaining a desired temperature inside of the first reactor, a stirrer for continuous mixing of the biowaste, a pH sensor, and at least one first input for providing a first set of ingredients for controlling pH of the biowaste in the first reactor; and a second reactor, arranged downstream from the first reactor, to receive the growth media from the first reactor for growing microbial mass, wherein the second reactor comprising an inoculum of microbial mass, a second inlet for receiving a second set of ingredients for growing microbial mass, the second set of ingredients comprising gases, water, and chemicals, and an outlet for harvesting the grown microbial mass from the second reactor.

In yet another aspect, an embodiment of the present disclosure provides a process for growing microbial mass in non-gravitational field conditions, wherein said process comprising culturing at least one isolated microbe, comprising culturing said at least one isolated microbe in continuous culture with hydrogen as energy source and carbon dioxide as the inorganic carbon source.

Embodiments of the present disclosure substantially eliminate or at least partially address the aforementioned problems in the prior art, and enable effective recovery of inorganic materials from the biowaste, comprising a wide variety of biological waste including, but not limited to, faeces and urine. The biowaste is used for optimal growth of micro-organisms in the closed-cycle system. Additionally, the embodiments of the present disclosure enable production of nutrients that can be utilized in nutraceuticals, pharmaceuticals, feed, food and/or food ingredients.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
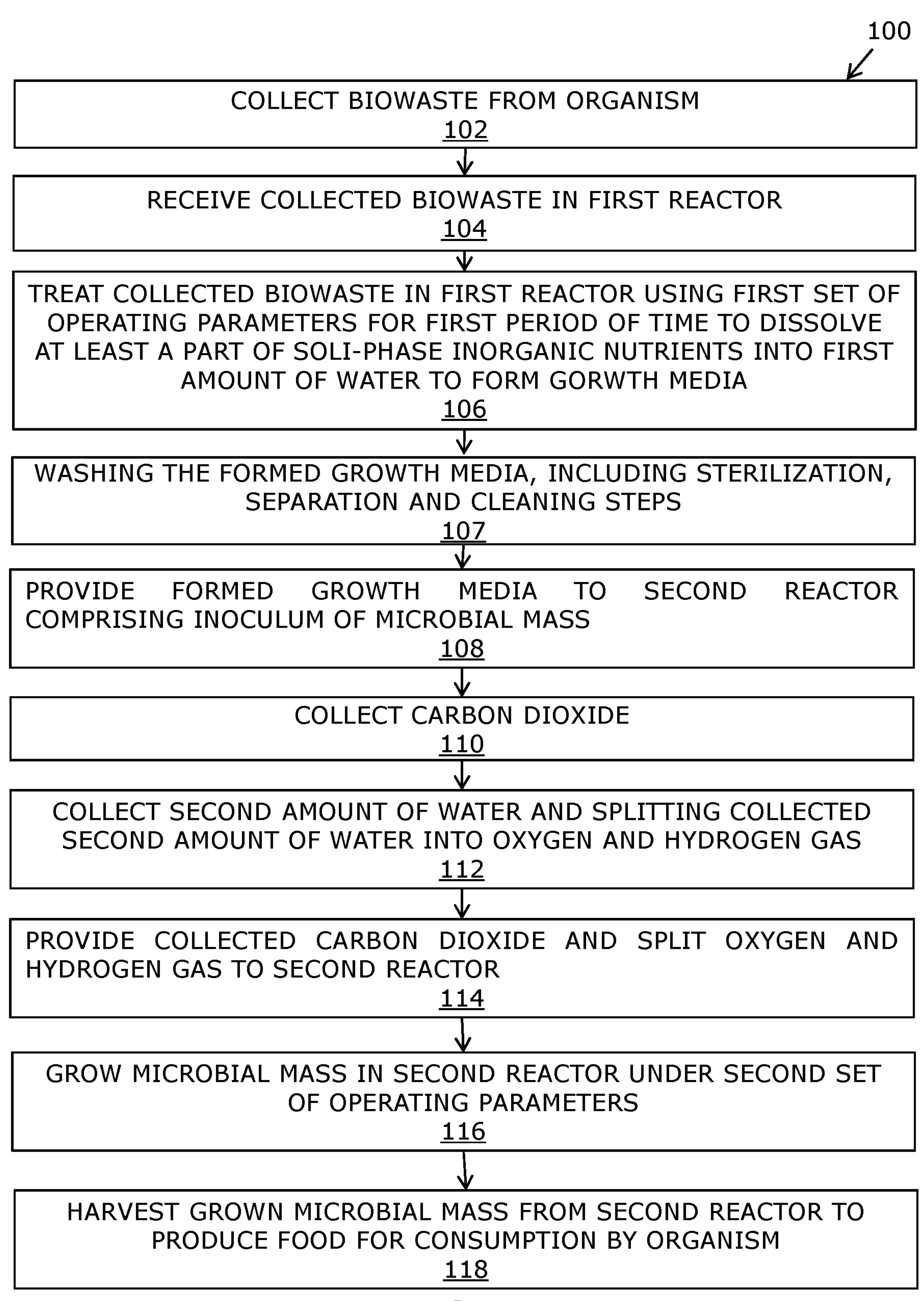
FIG. 1 is a flowchart depicting steps of a method for growing microbial mass, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a method of growing a microbial mass, the method comprising collecting biowaste from an organism, the biowaste comprising a first amount of water and a first amount of solid-phase;

receiving the collected biowaste in a first reactor;

treating the collected biowaste in the first reactor using a first set of operating parameters for a first period of time to dissolve at least a part of solid-phase inorganic nutrients into the first amount of water to form a growth media;

washing the formed growth media, wherein said washing includes sterilization, separation and cleaning steps;

providing the formed growth media to a second reactor comprising an inoculum of microbial mass;

collecting carbon dioxide locally from an atmosphere;

collecting a second amount of water present in the atmosphere and splitting the collected second amount of water into oxygen and hydrogen gas;

providing the collected carbon dioxide and the split oxygen and hydrogen gas to the second reactor;

growing a microbial mass in the second reactor under a second set of operating parameters; and harvesting the grown microbial mass from the second reactor to produce food for consumption by the organism.

In another aspect, an embodiment of the present disclosure provides a system for growing microbial mass, the system comprising a first stage configured to collect biowaste from an organism, the biowaste comprising a first amount of water and a first amount of solid-phase, wherein the first stage is a collector unit;

a first reactor connected to the first stage to receive the collected biowaste from the first stage via an inlet, treat the received biowaste therein to form a growth media, and wash the formed growth media, wherein said washing includes sterilization, separation and cleaning, and wherein for treating the biowaste the first reactor comprising a temperature controller for maintaining a desired temperature inside of the first reactor, a stirrer for continuous mixing of the biowaste, a pH sensor, and at least one first input for providing a first set of ingredients for controlling pH of the biowaste in the first reactor; and a second reactor, arranged downstream from the first reactor, to receive the growth media from the first reactor for growing microbial mass, wherein the second reactor comprising an inoculum of microbial mass, a second inlet for receiving a second set of ingredients for growing microbial mass, the second set of ingredients comprising gases, water, and chemicals, and an outlet for harvesting the grown microbial mass from the second reactor.

In yet another aspect, an embodiment of the present disclosure provides a process for growing microbial mass in non-gravitational field conditions, wherein said process comprising culturing at least one isolated microbe, comprising culturing said at least one isolated microbe in continuous culture with hydrogen as energy source and carbon dioxide as the inorganic carbon source.

The present disclosure provides the aforementioned method for growing microbial mass in a closed-cycle system by utilizing biowaste for producing food for consumption by humans (and/or animals). The method of the present disclosure comprises treating of biological waste before using it for growing microbial mass. Beneficially, the treatment process of the biological waste retains the chemical composition of the inorganic minerals of the biowaste such that the minerals remains available for the microorganisms to utilize in nutrient circulation inside the closed-cycle system. Therefore the treatment process enables effective nutrient circulation inside the closed-cycle system. Additionally, the method of the present disclosure removes pathogenic bacteria and toxins from the biowaste thereby enabling utilization of a wide variety of biological waste including, but not limited to, faeces and urine, for growing microorganism, thereby solving the problem associated with disposal of such waste material. Also, such microorganism can be used for example for food production, as safety is ensured by removing pathogenic bacteria and toxins.

Throughout the present disclosure, the term "microbial mass" as used herein refers to a measure of amount of living component (namely, microbes) in a sample, such as a culture media. Typically, microbes may include algae, bacteria, cyanobacteria, yeasts, fungi, archaea and the like. Mostly, microbes like bacteria, algae, and fungi decompose biowaste residues to release nutrients (such as nitrogen, carbon, and so on) and gases (carbon dioxide, hydrogen, methane, and so on). Moreover, the microbial mass have ability to metabolize toxins and xenobiotics, and bioaccumulate metal ions (such as zinc, copper, nickel, chromium, lead and the like) present in a sample. Notably, the microbes have the ability to grow in different types of growth conditions ranging from aerobic to anaerobic, and facultative conditions. As an alternative wording for the microbial mass a term a microbial biomass can be used.

It will be appreciated that the microorganisms grow in their suitable natural environments and/or artificial systems. The artificial system is configured to mimic the natural environment suitable for a given microorganism. Typically, an inoculum (i.e. a small amount of microorganisms as a seed culture) of microbes that works as starting material is used for growing more microbes under optimal growth conditions in the artificial system. Optionally, the artificial system is used to culture prokaryotic and eukaryotic cells, including plant cells, fungus, hybridoma cell lines and so forth. Initially, the artificial system is seeded with a volume of inoculum from an aseptically maintained microbial culture. Further, the microorganisms are allowed to grow, in a controlled environment, for a defined period of time to achieve an optimum growth, referred to as 'microbial mass' hereafter. The optimal growth of the microorganisms pertains to its biomass or by-product of the microbial growth, to be subsequently harvested for later use, such as for example in human nutrition including proteins, lipids, carbohydrates, vitamins, minerals, fibre, and so forth.

Optionally, the artificial system is implemented as a bioreactor for example. The term "bioreactor" refers to a vessel intended for biological and/or biochemical reactions required for culturing cells, growing micro-organisms, and production of biomolecules serving to meet nutritional, pharmaceutical or energy needs of consumers, under defined and controlled physical and chemical conditions. The bioreactor may have a shape such as cylindrical, conical, cuboidal or cubical. Optionally, the volume of the bioreactor is for example 10 litres, 100 litres, 200 litres, 1000 litres (L), and so forth.

Optionally, the bioreactor is fabricated from a material that is inert to contents to be processed in the bioreactor. In an example, the fabrication material may be stainless steel (for example type 304L, 316L or 316L), other suitable metals or alloys, glass material, fibres, ceramic, plastic materials and/or combinations thereof. Moreover, the fabrication material is typically waterproof and strong enough to withstand abrasive effects of various biological, biochemical and/or mechanical processes, such as micro-organisms concentrations, biomass productions, agitation forces, aeration forces, operating pressures, temperatures, acids, alkali and so forth. Typically, the bioreactor has an adequate thickness to hold a weight of the contents therein, and carry out various biological, biochemical and/or mechanical processes. Furthermore, the bioreactor should preferably be such that it withholds the sterilisation conditions, for example steam sterilisation with water vapour at 121° C. and a pressure of 2.5 bar. Alternatively the sterilization can be conducted using chemical sterilization or gamma sterilization.

The method of growing microbial mass initiates with collecting biowaste from an organism, the biowaste comprising a first amount of water and a first amount of solid-phase. Throughout the present disclosure, the term "biowaste" as used herein refers to a biodegradable waste composed mainly of organic matter. Typically, the biowaste includes food waste, green waste (such as refuse from gardens such as grass clippings, leaves, kitchen waste, that have high content of nitrogen therein), brown waste (such as dried leaves, pine straw, hay, sawdust, twigs, and so on, that have high content of carbon therein), animal effluent (such as feces, milk, urine, uterine discharge, saliva, and so on), and digestive waste (such as human excreta, namely urine and feces) that can be composted. The biowaste of the present disclosure is composed, primarily, of digestive waste, collected from an organism, such as a human and/or animal accompanying the human. Furthermore, such biowaste comprises pathogenic bacteria and toxins that may be a health risk for both people and animals. Pathogenic bacteria may comprise for example *Salmonella, E. coli, Salmonella, Shigella*, and *Vibrio* and other microorganisms, which may cause unpleasant and harmful infections. Pathogenic bacteria and/or toxins therefore need to be removed from the biowaste before growing the microbial mass for producing food.

Optionally, biowaste comprises feces and urine and the first amount of water is 50-90 weight percent of the biowaste. Notably, the feces form the first amount of solid-phase and the first amount of water is made up of urine, water-content corresponding to the feces, and/or flush water forming feces slurry. The first amount of water may form 50, 55, 60, 65, 70, 75, 80 or 85 weight percent up to 55, 60, 65, 70, 75, 80, 85 or 90 weight percent of the biowaste. In an example, the first amount of water is 90 weight percent of the biowaste. It is important to control amount of water in the bio-waste to ensure proper growing environment in the process. Furthermore, nitrogen, iron, calcium, phosphorus, manganese are elements that are found in large amounts in feces instead or in addition to urine. Recovery of these inorganics as nutrients is beneficial for growing the microbial mass for various purposes.

Moreover, the biowaste is collected in a collector unit (referred to as the "first stage" hereafter), within the aforesaid system for growing the microbial mass or as a separate arrangement coupled to the aforesaid system for growing the microbial mass. Typically, the first stage comprises at least one inlet and outlet to allow the contents thereof to flow into the first stage and subsequently into a downstream receiving chamber (referred to as the "first reactor" hereafter), respectively. Optionally, the first stage comprises a coarse filter in the at least one inlet and outlet to remove coarse suspended particles that may interfere with the efficient working of the system.

Subsequently, the collected biowaste is received in a first reactor. The term "first reactor" as used herein refers to a chamber or vessel, arranged inside the bioreactor or provided as a separate unit coupled to the bioreactor, configured to process the collected biowaste. The first reactor provides conditions suitable for processing the biowaste for its subsequent use for growing microbial mass. The first reactor typically is a three-dimensional hollow structure or container having a specific volume and a specific shape such as cylindrical, conical, cuboidal or cubical.

The collected biowaste in the first reactor is treated using a first set of operating parameters for a first period of time to dissolve at least a part of solid-phase inorganic nutrients into the first amount of water to form a growth media. In this regard, the first reactor is configured to be filled with the biowaste to a pre-defined level. Optionally, the pre-defined level of the biowaste in the first reactor may relate to a state when the biowaste is effectively processed to dissolve at least a part of solid-phase inorganic nutrients into the first amount of water using the first set of operating parameters to form slurry-like growth media.

Throughout the present disclosure, the term "growth media" as used herein refers to a fluid or semi-solid substrate providing nutrition for growing microbial mass. The growth media includes liquid-phase and solid-phase with or without nutrients. Optionally, the liquid-phase of the growth media comprises water and/or urine, and the solid-phase comprises of feces and solid-phase inorganic nutrients. It will be appreciated that normally the urine is about 90 weight percent of water and 10 weight percent of inorganic salts and organic compounds. The dry solids of urine comprise carbon, nitrogen, phosphorus, potassium, urea and ammonia. Moreover, the feces comprise about 75 weight percent of water and 25 weight percent of solid matter. Additionally, the solid matter comprises about 30 weight percent of microbes (bacteria, protozoa, parasitic worm eggs, and so on), 30 weight percent of indigestible food, 10-20 weight percent of fats, 2-3 weight percent of proteins, and 10-20 weight percent of inorganic nutrients. The inorganic nutrients obtained from feces are a source of carbon, nitrogen, calcium, phosphorus, iron, potassium, magnesium, selenium, and so forth. Beneficially, dissolving at least a part of the solid-phase inorganic nutrients into the first amount of water enables effective uptake of the inorganic nutrients for the growth of microbes thereon.

Optionally, the growth media may comprise added inorganic nutrients, including carbon, magnesium, potassium, phosphorus, sulphur, iron, zinc, manganese, nitrogen (for example in the form of ammonia, urea, nitrate, nitrite, amino acids, proteins (soluble, insoluble or hydrolysed)), animal by-products, dairy wastes, yeast, fatty acids, alcohols, polysaccharides, minerals, vitamins, growth factors, acids, bases, antibiotics, anti-foam agents, surfactants and the like. Optionally, the growth media further comprises gases such as oxygen, carbon dioxide, carbon monoxide, nitrogen, hydrogen, inert gases, oxides of nitrogen, methane, and so forth. It will be appreciated that apart from growth media the micro-organisms require gases for optimal growth.

Moreover, the first reactor contains the growth media, when in operation. It will be appreciated that the term "when in operation" used in the present disclosure is to be interpreted to not limit the first reactor only when it is operated by a given user but is intended to include both a structural as well as functional aspect of the first reactor.

Optionally, the first reactor may be implemented as a hydrothermal carbonization pressure vessel. The term "hydrothermal carbonization" or "HTC" as used herein refers to a thermochemical process, with temperature, pressure and pH control, for conversion of constituents (organic and inorganic compounds) of wet biowaste to energy and/or chemical compounds (such as structured carbons, biofuels, and so forth) without requiring pre-drying of the biowaste. HTC typically involves use of moderate temperatures, pressures and pH for treating the biowaste and for recovery of inorganic nutrients, such as nitrogen, iron, calcium, phosphorus, manganese, from both solid-phase (feces) and liquid-phase (urine). Optionally, HTC also involves parameters such as residence time, heating rate, concentration of the biomass, aqueous quality, and so forth. HTC enables to recover inorganic nutrients for growing the microbial mass for various purposes.

Optionally, the first reactor is an HTC-compatible pressure vessel, such as for example 10 L Hastelloy C276 pressure reactor. The first reactor uses ceramic heating element (6 kW). Optionally, the heating is provided from outside surface of the first reactor, such as by arranging the ceramic heating element around the first reactor along its outer surface. Alternatively, the heating is provided from inside surface of the first reactor, such as by arranging the ceramic heating element around the first reactor along its inner surface.

Optionally, the first set of operating parameters comprises of a temperature inside of the first reactor, wherein the temperature is at least 190 degrees Celsius; a pH of the growth media, wherein the pH is less than 4. The term "first set of operating parameters" as used herein refers to a set of conditions required for treatment of the biowaste in order to dissolve at least a part of the solid-phase inorganic nutrients into the first amount of water for growing microbial mass. The first set of operating parameters comprises temperature, pH and pressure condition inside the first reactor. It will be appreciated that the temperature conditions, pressure and pH value of the content of the first reactor are important parameters to ensure the breaking of the solid matter as well as maintaining the integrity of the solid-phase inorganic nutrients. The temperature may for example be from 150 degrees Celsius (° C.), 160° C., 170° C., 180° C., 190° C., 200° C., 210° C., 220° C., 230° C., 240° C. or 250° C. up to 160° C., 170° C., 180° C., 190° C., 200° C., 210° C., 220° C., 230° C., 240° C., 250° C. or 300° C., preferably from 180° C., 190° C., 200° C., 210° C., 220° C., 230° C. or 240° C. up to 190° C., 200° C., 210° C., 220° C., 230° C., 240° C. or 250° C., more preferably from 190° C., 200° C. or 210° C. up to 200° C., 210° C. or 220° C. In an example, the temperature is 220° C. The above-mentioned temperature range is beneficial in killing pathogenic bacteria in the growth media that may be deleterious to the growth media and the microbial mass growing thereon, as well as toxic to the final consumers of the said microbial mass. Moreover, the aforementioned temperature range enables breaking the solid-phase organic matter into an appropriate form. It will be appreciated that the temperature should not be very high since the first reactor is a pressure vessel and may be hazardous to use at very high temperatures. Moreover, the growth media may boil at very high temperatures. The pH may for example be an acidic pH ranging from, for example, 2, 2.5, 3 or 3.5 up to 2.5, 3, 3.5 or 4. In an example, the pH is 2.3. Optionally, the pH of the content of the first reactor is adjusted using an acid, such as for example, sulfuric acid. It will be appreciated that the lower pH conditions during the HTC process results in more soluble solid-phase inorganic nutrients in the liquid-phase, i.e. the first amount of water. The pressure may be from 10, 12, 14, 16 or 18 bars up to 12, 14, 16, 18 or 20 bars. In an example, the pressure is 10 bars.

Optionally, the method further comprises stirring the biowaste in the first reactor at a speed of at least 100 RPM. It will be appreciated that stirring the biowaste results in breaking the solid matter of the biowaste in smaller particles thereby causing effective dissolution of the solid-phase inorganic nutrients in the first amount of water to form the growth media. Additionally, stirring the biowaste results in efficient aeration of the biowaste and thereby preventing a hazardous blast in the first reactor. The stirring speed may typically be for example 100 RPM, 200 RPM, 500 RPM, 1000 RPM, 2000 RPM, and so forth. Optionally, the stirring speed is 200 RPM. Optionally, stirring of the biowaste may be unidirectional or a whirlpool action.

Optionally, the first period of time is one hour to 18 hours. The treatment of the biowaste in the first reactor by employing HTC process is performed for a predetermined period of time, i.e. the first period of time. The term "first period of time" as used herein refers to a duration of time required for substantial dissolution of a part of the solid-phase inorganic nutrients into the first amount of water to result in a suitable growth media for growing microbial mass thereon. The first period of time may typically range from 1, 1.5, 2, 3, 6, or 12 hours up to 2, 3, 6, 12 or 18 hours. In an example, the first period of time is 1 hour. It will be appreciated that the first period of time is a function of speed of the stirring the biowaste. In this regard, for a high speed of stirring the first period of time is less, and for a low speed of stirring the first period of time is more. Additionally, optionally, the first period of time is a function of temperature inside the first reactor. In this regard, for a high temperature of the first reactor, the first period of time required for treating the biowaste is shorter, and for a low temperature of the first reactor, the first period of time required for treating the biowaste is higher.

Beneficially, HTC enables recovering the inorganic nutrients, such as nitrogen, iron, calcium, phosphorus, manganese, from the biowaste without involving energy-intensive drying process and/or compensating for the structural or functional integrity of the desired inorganic nutrient opposed to the conventional ash-forming method or chemical processes involving hours of treatment in presence of acids. Additionally, beneficially, the heat produced during the exothermic reaction in the first reactor contributes to the temperature conditions therein, thereby significantly reducing the energy consumption required for maintaining the temperature conditions inside the first reactor. Moreover, the HTC process is time-efficient.

Optionally, the amount of water in the growth media is adjusted by adding a third amount of water to the first reactor if the amount of water in the growth media is less than 20 weight percent of the growth media, and adding more solid-phase if the amount of water in the growth media is more than 20 weight percent of the growth media. Notably, the growth media of a pre-defined concentration (i.e. the first amount of water and the first amount of solid-phase) and consistency is required for growing microbial mass. In this regard, the concentration and consistency of the growth media may be suitably altered, my adjusting the amount of water therein, in the first reactor. The pre-defined concentration of the growth media comprises 20 weight percent of the amount of water and 80 weight percent of the solid-phase. Therefore, the growth media may be suitably diluted or concentrated using the third amount of water if the amount of water in the growth media is less than 20 weight percent of the growth media and adding more solid-phase if the amount of water in the growth media is more than 20 weight percent of the growth media, respectively. Optionally, the third amount of water may be obtained from urine or normal water. According to alternative embodiment the limit of adding the third amount of water or adding more solid-phase material can be between 15-25 weight percent.

The method further comprises washing the formed growth media prior to providing the formed growth media to the second reactor. The term "washing" as used herein refers to cleaning of the growth media from pathogenic bacteria and toxins present in biowaste. Washing (or cleaning) the growth media includes sterilization, separation and cleaning steps. In this regard, the growth media comprising dissolved at least a part of solid-phase inorganic nutrients into the first amount of water, is subjected to sterilization and separation steps in order to kill pathogenic bacteria and other toxins from the growth media and separate undissolved solid phase in the growth media, respectively. Notably, sterilization and separation steps are performed before the growth media is introduced into the growth chamber, referred to as the "second reactor" hereafter. Indeed since a process such as pyrolysis or combustion is not used in present disclosure it is possible to recover inorganic materials such as nitrogen, iron, calcium, phosphorus, manganese. Optionally, the separation step utilizes a filter (namely, screen, mesh or membrane) to separate the undissolved solid phase in the growth media. More optionally, the filter (namely, screen, mesh or membrane) is arranged at an outlet of the first reactor that opens into the second reactor. The separation step may utilize membrane separation techniques such as microfiltration, ultrafiltration, nanofiltration and reverse osmosis. The cleaning step of the present disclosure comprises washing of carbonized residue (resulting from the HTC process) in the growth media. The said washing of the carbonized residue is important for further improving the recovery of salts and nutrients in the liquid phase of the growth media. Optionally, the cleaning step is performed by washing with water (deionized water, distilled water, hot water, or cold water), with or without agitation, for example. Alternatively, optionally, the cleaning step is performed by washing with chemicals, such as for example hydrochloric acid, nitric acid, sulfuric acid, sodium hydroxide, alkali, and the like.

The method comprises providing the formed growth media to a second reactor comprising an inoculum of microbial mass. The term, "second reactor" as used herein refers to a chamber or vessel arranged downstream from the first reactor. The second reactor is configured for growing microbial mass in the growth media received from the first reactor. The second reactor provides conditions suitable for growing microbial mass. Optionally, the second reactor is vertically positioned lower to the first reactor. The aforesaid arrangement enables the growth media to flow from the first reactor to the second reactor. The growth media flows from the first reactor to the second reactor due to effect of gravity. Optionally, the first reactor is positioned on top of the second reactor in a manner such that both the first and second reactors share a common vertical axis. Alternatively, the first reactor may be positioned on top of the second reactor such that they do not share the common vertical axis, i.e. the second reactor is positioned adjacent and downstream from the first reactor. In such a case, the first and the second reactors are vertically spaced apart. In another embodiment, the second reactor is not positioned below the first reactor, rather vertically spaced apart such that a top surface of the second reactor is above a bottom surface of the first reactor. Optionally, before providing the formed growth media to the second reactor, the growth media can be filtered using for example a membrane.

Optionally, the second reactor typically is a three-dimensional hollow structure or container having a specific volume and a specific shape such as cylindrical, conical, cuboidal or cubical. Optionally, the first and second reactors are structurally similar to each other, for example, based on volume, dimension, fabrication material thereof, and the like. Alternatively, the first and second reactors may be structurally dissimilar. It will be appreciated that first and the second reactors may be functionally similar or dissimilar to each other.

Moreover, the second reactor during operation includes the inoculum of microbial mass in at least one growth phase of a lag phase (where the growth of the microbial mass is about to start or just started), a log phase (where growth of the microbial mass is increasing at a fast rate), or a stationary phase (where growth of the microbial mass has stopped or is about to stop). Optionally, the system of the present disclosure is a continuous cultivation system where growth media is added constantly and growth media is removed constantly, the growth of the microbial mass can reach a steady-state where the growth rate is constant. Optionally, the inoculum of microbial biomass comprises at least one isolated microbe, wherein said microbe has ability to grow using hydrogen gas as energy source and carbon dioxide as an inorganic carbon source.

Optionally, the isolated microbe may be obtained from a natural habitat thereof. Alternatively, optionally, the isolated microbe may be obtained from a laboratory culture thereof, where it is produced and stored under the guidelines of Good Manufacturing Process (GMP) and sterile conditions. The isolated microbes have ability to utilize hydrogen gas and carbon dioxide as the energy and carbon sources, respectively. Based on the carbon source, the microbes may be autotrophs (carbon is obtained from carbon dioxide), heterotrophs (carbon is obtained from organic compounds) or mixotrophs (carbon is obtained from both organic compounds and by fixing carbon dioxide). Based on the energy source, the microbes may be autotrophs, photoautotrophs (energy is obtained from sunlight), lithotrophs (electron acceptors, such as hydrogen, are obtained from inorganic compounds), organotrophic (electron acceptors, such as hydrogen, are obtained from organic compounds), or chemotrophs (energy is obtained from external chemical compounds). It will be appreciated that in practice, the aforesaid terms may be freely combined to refer to microbes based on their energy and carbon sources, such as for example chemolithotrophs, chemolithoautotrophs, chemolithoheterotrophs, and so forth.

Optionally, the microbes for the inoculum are selected from a group of: *Clostridium ljungdahlii, Saccharomyces cerevisiae*, Knallgas bacteria (such as *Cupriavidus necator, Rhodococcus opacus, Hydrogenobacter thermophilus, Hydrogenovibrio marinus, Alcaligenes eutropha*, and so on), genus *Caminibacter*, genus *Aquifex*, genus *Paracoccus*, genus *Xanthobacter*, genus *Hydrogenomonas*, methanotrophs, methanogens, genus *Geobacter*, genus *Cyanobacterium*, genus *Acetobacterium*, genus *Oscillospira*, genus *Pleomorphomonas*. *Clostridium ljungdahlii* is an anaerobic homoacetogen growing on synthesis gas and carbon dioxide/hydrogen mixtures. *C. ljungdahlii* is able to ferment sugars, other organic compounds, carbon dioxide/hydrogen mixtures and/or synthesis gas to produce proteins and chemicals. In the process *C. ljungdahlii* enables sustained reduction of carbon dioxide and carbon monooxide in the atmosphere. Knallgas bacteria are known to utilize oxygen to fix carbon dioxide and oxidize hydrogen gas to grow their biomass under chemolithoautotrophic conditions. The Knallgas bacteria under aerobic or facultative chemolithoautotrophic conditions produce proteins and other high-energy molecules. Microbes belonging to the genus *Caminibacter* are thermophilic, anaerobic, chemolithoautotrophic bacteria. They utilize hydrogen gas and carbon dioxide as energy and carbon sources respectively for growth thereof. Microbes belonging to the genus *Aquifex* are extreme thermophiles growing best at temperature ranging from 85° C. to 95° C., and in aerobic (levels of oxygen being very low) or anaerobic conditions by reducing oxygen or nitrogen respectively. Microbes belonging to the genus *Paracoccus* are facultative bacteria having ability to reduce nitrates into molecular nitrogen. *Paracoccus* species are able to use a variety of organic and inorganic substrates for their growth, thus find potential use in bioremediation processes. Microbes belonging to the genus *Xanthobacter* are nitrogen-fixing organisms, that could grow chemolithoautotrophically (using molecular nitrogen as nitrogen source under presence of hydrogen, carbon dioxide and oxygen in their environment) as well as chemoorganoheterotrophically (using methanol, ethanol and various organic acids as sole carbon sources). Microbes belonging to the genus *Hydrogenomonas* are a group of facultative autotrophs that could use hydrogen as electron donor. Methanogens are anaerobic organisms that produce methane as a metabolic by-product in hypoxic conditions, and thus find application in wastewater treatment. Microbes belonging to the genus *Geobacter* are anaerobic bacteria that oxidize organic compounds and metals into carbon dioxide, thus find application in biodegradation and bioremediation. Microbes belonging to the genus *Cyanobacterium* are both free-living photosynthetic bacteria and endosymbiotic bacteria. *Cyanobacterium* species are known to fix atmospheric nitrogen into ammonia, nitrates or nitrites, that are eventually converted to proteins, under anaerobic conditions. Microbes belonging to the genus *Acetobacterium* are anaerobic bacteria that use carbon dioxide or carbon monoxide to produce acetate. Microbes belonging to the genus *Oscillospira* are anaerobic organisms using sugars as carbon source. Microbes belonging to the genus *Pleomorphomonas* utilize methane as carbon and energy source. *Pleomorphomonas* species can also fix nitrogen. *Saccharomyces cerevisiae* is a facultatively anaerobic yeast that causes fermentation of sugar (such as glucose, maltose, trehalose, and so on) to yield proteins and other useful compounds (such as bioethanol). Methanotrophs are methane-utilizing bacteria known to be able to grow in the presence of oxygen to produce proteins and chemicals as part of microbial mass.

Optionally, the growing of the microbial mass comprises culturing a bacterial strain of the genus *Xanthobacter* in continuous culture with hydrogen as energy source and an inorganic carbon source, wherein the inorganic carbon source comprises carbon dioxide. As mentioned above, bacterial strain of the genus *Xanthobacter* is a nitrogen-fixing bacteria, that fixes nitrogen in the presence of hydrogen as energy source and carbon dioxide as the carbon source. Initially, the bacterial strain of the genus *Xanthobacter* is inoculated in the second reactor to grow in a continuous culture for a predefined period of time and/or until the microbial mass has grown to a pre-determined size.

Optionally, the microbial mass comprises an isolated bacterial strain VTT-E-193585 or a derivative thereof, wherein said derivative has retained the ability to grow using hydrogen gas as energy source and carbon dioxide as the only carbon source. Strain VTT-E-193585 (SoF1) has been deposited on Jun. 11, 2019 in the VTT Culture Collection at the VTT Technical Research Centre of Finland, P.O. Box 1000, FI-02044 VTT, Finland, an International Depositary Authority under the Budapest Treaty. The isolated bacterial strain VTT-E-193585 or a derivative thereof is genetically stable and can be grown in a broad range of process conditions, ranging from optimal to stressful conditions, over time, by utilizing hydrogen gas as energy source and carbon dioxide as carbon source. The term "genetically stable" as used herein, refers to a characteristic of a species or a strain/isolate to resist changes and maintain its genotype over multiple generations or cell divisions, ideally hundreds to thousands.

The method comprises collecting carbon dioxide. As the microbes use carbon dioxide as a carbon source for growth thereof, carbon dioxide is collected from the atmosphere or alternatively supplied from other processes. It will be appreciated that carbon dioxide can be collected using various techniques known to a person skilled in the art. In particular, in systems, such as closed-cycle systems, the carbon dioxide is collected locally from the atmosphere, such as that covered by walls of said systems. For example, carbon dioxide may be collected using chemical media, functional sorbents, or carbon dioxide extractors. Beneficially, microbes continuously utilizing carbon dioxide from the atmosphere result in consuming the amount of carbon dioxide in the atmosphere. Since, the human occupants of said systems respire to generate more and more carbon dioxide as the respiratory by-product thereof for the utilization of the respired carbon dioxide by the microbes, the carbon dioxide from the atmosphere never ends, thus serves as a readily available carbon source for the microbes to grow. Optionally, alternatively, the carbon dioxide and energy are obtained from external atmosphere, such as via the solar panels, in such case the system may be a regenerative system.

Optionally, the method further comprises extracting carbon dioxide from at least a part of the growth media. In this regard, the carbon dioxide is fixed from the growth media. Moreover, inorganic carbon (in the form of carbon dioxide) from the growth media is fixed or converted to organic compounds by microbes. The organic compounds are then used to store energy required by microbes for their growth.

The method comprises collecting a second amount of water and splitting the collected second amount of water into oxygen and hydrogen gas. The term "second amount of water" as used herein refers to an amount of water or moisture present in the atmosphere. It will be appreciated that the occupants of the system, such as humans, respire to produce carbon dioxide and water vapors in the atmosphere. The second amount of water is typically collected from the local atmosphere by condensing moisture in the atmospheric air, urea, and so forth. The collected second amount of water is split, such as using electrolysis process, into hydrogen gas and oxygen. Hydrogen gas released in the process is utilized by the microbes as energy source for growth thereof. Moreover, oxygen produced by splitting of the second amount of water improves the rate of hydrolysis of the organic matter of the growth media by facultative or aerobic microbes. Beneficially, the splitting of the second amount of water into hydrogen gas and oxygen removes the requirement to install gas-phase containers for storing hydrogen gas and oxygen to be made available for growing microbial mass.

The method comprises providing the collected carbon dioxide and the split oxygen and hydrogen gas to the second reactor. It will be appreciated that apart from growth media the microbes require gases for optimal growth. The gases are dissolved in the growth media inside the second reactor. The split oxygen and hydrogen gas and collected carbon dioxide are supplied to the second reactor to provide aeration and necessary energy and carbon source to the microbial mass in the second reactor. Moreover, oxygen is provided to the microbes in dissolved form. Typically, the dissolved oxygen is provided to microbes continuously through a process called aeration. Dissolving gases in the growth media is proportional to residence time of gases. Throughout the disclosure, the term "residence time" as used herein refers to a duration of time which the gases spend in a bioreactor. In an example, the residence time of a gas, in the form of a gas bubble, in the growth media may range from 10 to 30 minutes. Optionally, small gas bubbles have higher surface area per volume as compared to large gas bubble and therefore have less buoyancy and therefore have longer residence time. Optionally, the said gases may be sparged into the growth media to enable effective mixing of the gases with the growth media and increasing the residence time of each gas in the growth media for efficient utilization by the microbes. It will be appreciated that aeration of the growth media enables maintaining freshness of the growth media resulting in effective microbial growth. Optionally, other gases, apart from carbon dioxide, oxygen and hydrogen gas may be provided to the second reactor. The other gases include, but are not limited to, carbon monoxide, nitrogen, inert gases, oxides of nitrogen, methane, and so forth.

Typically, the gases are provided to the second reactor based on a predetermined quantity, which is based on a quantity of microbes present in the growth media. In other words, based on a desired quantity of the microbial mass to be grown and knowing the ability of the microbes to utilise the gases, the quantity of gases and the growth media is decided. Optionally, the amount of gases depends on different lengths of the growth phase of the microbes. Optionally, the amount of gases depends on strategies utilized for growing of microbial mass, such as aerobic growth, anaerobic growth, facultative growth, and so forth.

The method comprises growing a microbial mass in the second reactor under a second set of operating parameters. The second reactor is configured with the second set of operating parameters that enable efficient growing of microbial mass. The term "second set of operating parameters" as used herein refers to a set of conditions required for growing microbial mass in the second reactor. The second set of operating parameters comprises nutritional requirements as provided by the aforementioned growth media, aeration (dissolved oxygen concentration) and agitation (mixing achieved by stirring the growth media regularly), osmotic pressure, pH and temperature condition inside the second reactor. It will be appreciated that high growth rates of microbes result in rapid changes in the second set of operating parameters thereby requiring constant monitoring of the second set of operating parameters, such as for example via controller arrangements, regulators and/or sensors. The nutritional requirements typically include macromolecules (such as carbon, hydrogen, oxygen, nitrogen, sulfur, phosphorus) and micromolecules (such as trace elements and organic growth factors, for example as magnesium, potassium, sodium, calcium and iron). Moreover, the temperature range may vary for different types of microbes. Based on a preferred temperature range, the microbes are typically classified into psychrophiles (cold-loving microbes having optimum temperatures between 0-30° C.), mesophiles (moderate temperature-loving microbes having optimum temperatures between 25-40° C.) and thermophiles (heat-loving microbes having optimum temperatures between 50-80° C.). Furthermore, neutral pH ranging between 5.4 and 8.5 is best suited for microbial growth. However, some microbes, referred to as acidophiles, may grow in acidic pH (below 45.4) while others, referred to as alkalophiles, may grow in alkaline pH ranging between 7 and 14. Notably, molds and yeasts grow best at pH ranging between 5 and 6. Furthermore, growth of microbial mass is also a function of osmotic pressure (determined by salt concentration in the external environment of the microbe) of the growth media. Additionally, the growth media requires regular aeration and agitation in order to dissolve gases (such as oxygen) in the growth media for uptake by microbes. It will be appreciated that the growth media comprises sufficient liquid phase, such as water, to promote growing microbial mass. It will be appreciated that the inoculum of microbes in the second reactor is in an early lag and/or log growth phase.

The method comprises harvesting the grown microbial mass from the second reactor to produce food for consumption by the organism. The term "harvest" or "harvesting" as used herein refers to a process of removal of the grown microbial mass from the growth media in the second reactor. Optionally, the harvesting of the grown microbial mass is conducted either continuously or batch-per-batch. The grown microbial mass is normally in its stationary growth phase, i.e. when the microbes fail to grow any further. The harvested grown microbial mass may be processed further to derive desired products therefrom, using techniques known to a person skilled in the art. The desired products derived from the harvested grown microbial mass includes proteins, lipids, carbohydrates, fibre, vitamins, minerals and/or antioxidants. Optionally, the desired products may be consumed as food, food ingredients, a nutraceutical, a pharmaceutical, a consumable and/or application product, and so forth. In deed the method steps provide synergistic effect and enable growing of a microbial mass. According to an embodiment the method is suited for growing a microbial mass in a closed system such as in a space station since biowaste can be collected from an astronaut in the space station, the carbon dioxide can be collected from atmosphere of the space station and the harvested grown microbial mass can be provided as food for the astronaut thus closing the circle.

Optionally, the microbial mass is operable to recycle the biowaste and gases into food for consumption by the organism, and wherein the food is rich in at least one of: a protein, a carbohydrate, a fatty acid, an antioxidant, a fibre content. The microbes in their early lag and/or log growth phase utilize the organic compounds in the growth media and the gases provided to the second reactor to recycle the biowaste and gases into consumable products, preferably nutrients. Optionally, the microbial mass comprises of microbes which are able to produce proteins, lipids, carbohydrates, fibre, vitamins, minerals and/or antioxidants. It will be appreciated that the nutrients derived from the harvested microbial mass is safe for use by the organisms such as humans and animals alike, preferably by humans to meet the low-cost nutritional requirements.

Optionally, the method further comprises collecting urea from the organism, providing the collected urea to a third reactor for a treatment thereof and providing the treated urea from the third reactor to the second reactor as an additional growth media component for the growth of microbial mass. It will be appreciated that urea hydrolyses to provide urea nitrogen in the form of ammonia, and carbon dioxide. The microbes utilize the nitrogen in the presence of hydrogen, and oxygen from the growth media for growth thereof. Optionally, the third reactor is arranged parallel to the first reactor or alternatively, downstream of the first stage, to collect urea. Optionally, the third reactor is configured to treat the collected urea for rendering it safe for use as growth media. Optionally, the third reactor is a three-dimensional hollow structure or container having a specific volume and a specific shape such as cylindrical, conical, cuboidal or cubical. Optionally, the first, second and third reactors are structurally similar to each other, for example, based on volume, dimension, fabrication material thereof, and the like. Alternatively, the first, second and third reactors may be structurally dissimilar. It will be appreciated that first and third reactors may be functionally similar or dissimilar to each other.

The present disclosure also relates to the system as described above. Various embodiments and variants disclosed above apply mutatis mutandis to the system.

Notably, the first reactor is connected to the first stage by an inlet via which the collected biowaste from the first stage is received for treatment thereof in the first reactor. Optionally, the inlet is a tubular structure having a certain length, which acts as passage for providing the collected biowaste from the first stage to the first reactor. Further, a pump may be employed to allow the flow of the collected biowaste from the first stage to the first reactor. Additionally, the inlet may be operatively coupled to a regulator for regulating supply of the collected biowaste via the inlet into the first reactor.

The first reactor, for the treatment of the received biowaste, comprises a temperature controller for maintaining a desired temperature inside of the first reactor, a stirrer for continuous mixing of the biowaste, a pH sensor, and at least one first input for providing a first set of ingredients for controlling pH of the biowaste in the first reactor. Optionally, the first reactor comprises a controller arrangement for controlling the first set of operating parameters inside the first reactor to provide controlled conditions for treating the biowaste. In this regard, the controller arrangement comprises a plurality of sensors and regulators (or a combination thereof) for sensing and regulating, based on the sensor data, the first set of operating parameters inside the first reactor. The controller arrangement includes for example a temperature controller, a humidity sensor, a gas concentration sensor, a pH sensor, and so on for detecting (or sensing) the temperature, the humidity, the gas concentration (relative concentrations of at least two of gases, such as carbon dioxide, oxygen, and other gases) and the pH within the first reactor, respectively. It will be appreciated that the at least one first input serves as entry points to the first reactor, from where the first set of ingredients, such as alkaline or acidic compounds or solutions, for controlling the pH of the biowaste in the first reactor are added. It will be appreciated that acidic compounds or solutions are added if the pH of the biowaste is more than the pre-defined pH value, for example more than 2.3, and alkaline compounds or solutions are added if the pH of the biowaste is less than the pre-defined pH value, i.e. more than 2.3, to bring the pH of the biowaste to a predefined range. Optionally, the controller arrangement is configured to sense and regulate the first set of operating parameters inside the first reactor continuously throughout the treatment time, or intermittently i.e. at predefined time durations, such as at time durations in a gap of at least one of: 5 minutes, 10 minutes, 15 minutes, 20 minutes, 30 minutes, 60 minutes, and so forth, for example or time between 1 hour to 18 hours or any range of as described earlier.

Optionally, the first set of operating parameters that are optimal for treating the biowaste is obtained from a database, wherein the database is communicably coupled to the controller arrangement. Furthermore, the database relates to an organized body of digital information regardless of a manner in which the data or the organized body thereof is represented. More optionally, the database may be hardware, software, firmware and/or any combination thereof. The database includes any data storage software and system, such as, for example, a relational database like IBM DB2 and Oracle 9. More optionally, the controller arrangement is communicatively coupled to the database via a communication network. In an example, the communication network includes but not limited to, a cellular network, short range radio (for example, such as Bluetooth®), Internet, a wireless local area network, and an Infrared Local Area Network, or any combination thereof.

The first reactor has a first outlet for providing treated biowaste in the form of growth media to the second reactor. The first outlet, similar to the first inlet, is a tubular structure having a certain length, which acts as an exit or passage for the growth media from the first reactor. Optionally, the first outlet may be operatively coupled to a regulator for regulating outflow of the growth media via the first outlet.

The second reactor comprises an inoculum of microbial mass, a second inlet for receiving a second set of ingredients for growing microbial mass, the second set of ingredients comprising gases, water, and chemicals, and an outlet for harvesting the grown microbial mass from the second reactor. The inoculum of microbial mass is typically fed to the second reactor once at the beginning of the process, via a feed inlet. It will be appreciated that apart from the growth media received from the first reactor, the microbes require other ingredients for their growth. The second set of ingredients are configured to provide the necessary elements required for growing microbial mass. The second set of ingredients comprises gases, such as oxygen, carbon dioxide, hydrogen gas, and so on, water, and chemicals such as alkaline and or acidic compounds or solutions for maintaining an optimum pH of the growth media.

Optionally, the second inlet is a tubular structure having a certain length, which acts as an inlet for providing the second set of ingredients to the second reactor. The second inlet may be provided on side walls of the second reactor. Further, the second inlet may be provided at a bottom end of the second reactor. The gases for the second inlet may be provided from a gas storage unit, which may be situated outside the second reactor. Further, a pump may be employed to allow the flow the gases from the gas storage unit to the second reactor. Additionally, the second inlet may be operatively coupled to a regulator for regulating supply of the gases via the second inlet into the second reactor. Optionally, the gases may be stored under pressure in the gas storage unit, i.e. in a compressed state. Moreover, a flowrate of the gases may be controlled by a controller arrangement, i.e. the controller arrangement may regulate a quantity and/or a velocity of the gases to be flown from the gas storage unit to the second reactor. In an example, a flowrate of gas is in a range of 0.1 to 2 volume of gas/volume of growth media/minute (vvm).

Optionally, the second inlet may comprise a nozzle having a number of openings for creating gas bubbles. The nozzle, for example, a sparger, may serve as a protrusion at the end of the second inlet, and comprises a number of openings, such as small holes, to disperse the gases as gas bubbles into the second reactor. The gases sparged through the number of openings of the nozzle results in a combination of small and large gas bubbles. Moreover, diameter of the openings in the nozzle can be for example 0.5-200 μm (micrometres), preferably 1-30 μm, more preferably 3-10 μm. The diameter of the openings in the nozzle can be for example from 0.5, 0.7, 1, 2, 3, 5, 7, 10, 15, 20, 22, 25, 30, 35, 40, 45, 50, 55, 60, 65, 70, 75, 80, 85, 90, 95, 100, 110, 120, 130, 140 or 150 μm up to 1, 2, 3, 5, 7, 10, 15, 20, 22, 25, 30, 35, 40, 45, 50, 55, 60, 65, 70, 75, 80, 85, 90, 95, 100, 110, 120, 130, 140, 150, 160, 170, 180, 190 or 200 μm. Optionally, shape of gas bubbles is any of tubular, spherical, hemispherical, ellipsoidal, semi-ellipsoidal and/or a combination thereof. The term "sparge", "sparged" or "sparging" refers to a process of injecting a gas into a liquid such as the growth media by employing the sparger (or a diffuser or a nozzle). Optionally, sparging is used to dissolve a gas into a liquid phase, such as in aeration and carbonation, for further reaction in applications such as fermentation, ozonation, oxidation, hydrogenation and so forth. Alternatively, sparging is used to remove contaminants from the growth media, such as in stripping applications and so forth.

Optionally, the second inlet comprises a plurality of passages, each for carrying an individual ingredient of the second set of ingredients to be provided to the second reactor. Notably, the second reactor may be provided with a plurality of separate second inlet for providing each of the second set of ingredients to the second reactor. Alternatively, the second reactor may be provided with a common second inlet for providing each of the second set of ingredients to the second reactor. In an example, in case of the second inlet for providing gases to the second reactor, the second inlet includes at least one separation making two or more passages for the two or more gases, wherein each of the plurality of passages acts as a dedicated input for carrying the individual gas of the gases to be provided to the second reactor. The dedicated inputs prevent mixing of the gases, which may cause undesirable reactions such as exothermic reaction. In an example, the second inlet comprises a first passage carrying oxygen gas, a second passage carrying carbon dioxide, a third passage carrying hydrogen gas, and so forth. Optionally, the second inlet may be formed by a group of second inlets arranged at different positions in the second reactor.

Optionally, each of the first reactor and the second reactor further comprises an agitator arrangement for mixing the biowaste and the growth media comprising microbial mass and the second set of ingredients therein. The stirrer is configured to agitate the biowaste in the first reactor to mix the liquid phase and solid phase of the biowaste to form growth media, as well as the growth media comprising microbial mass and the second set of ingredients in the second reactor. The term "stirrer" as used herein refers to a rotating device for mixing the biowaste to form a slurry of growth media and further mixing the growth media for aeration thereof. In an example, the stirrer is configured and operable to rotate in a clockwise direction, anti-clockwise direction or both. The stirring speed of the stirrer in the first reactor may typically be for example 100 RPM, 200 RPM, 500 RPM, 1000 RPM, 2000 RPM, and so forth. Optionally, the stirring speed is 200 RPM. Optionally, the stirrer comprises a motor, a shaft connected to the motor and blades arranged on the shaft. Optionally, the blades are anchor-type blades. The blades are rigidly coupled on the shaft of the agitator arrangement, and operable to rotate with the rotation of the shaft. Optionally, the blades comprise a group or a set of blades rigidly coupled to shaft in a vertically spaced apart manner. More optionally, each of the group of blades may include two or more blades.

Optionally, each of the first and the second reactors comprises a separate stirrer. Alternatively, the first and the second reactors may include a common stirrer, i.e. having a shaft running through both the first and the second reactors. Further, blades are coupled to the shaft and the shaft is coupled to a common motor (either directly or using a belt and pulley arrangement).

Moreover, the second reactor comprises an outlet for harvesting the grown microbial mass from the second reactor. Typically, the outlet, similar to the second inlet, is a tubular structure having a certain length, which acts as an outlet for the grown microbial mass from the second reactor. Optionally, the outlet may be operatively coupled to a regulator for regulating outflow of the growth media via the outlet. Optionally, the outlet may be provided on side walls of the second reactor. Further, the outlet may be provided at a bottom end of the second reactor. Optionally, a pump is employed to harvest the grown microbial mass from the second reactor. It will be appreciated that the grown microbial mass harvested from the second reactor has microbial mass in advanced growth phase, i.e. the log phase. Specifically, the gases provided by the second inlet majorly comes in contact with the growth media of the second reactor, allowing the microbes present in the growth media of the second reactor to substantially consume the gases and causes substantial growth thereof. Optionally, the growth media of the second reactor is constantly removed from the reactor to accommodate fresh growth media from the first reactor, to enable optimal growth of microbial mass in the second reactor. Optionally, the growth media removed from the second reactor is stored in an output growth media storage unit.

Optionally, the system further comprises a gas recycle arrangement, arranged between the first reactor and the second reactor for recycling the excess gases. It will be appreciated that the gas recycle arrangement essentially includes an elongate passage or tubular structure that fluidically couples the first reactor to the second reactor. Optionally, the gas recycle arrangement is coupled to the gas storage unit. The gas recycle arrangement may include valves and regulator for controlling the flow of excess gases. Additionally, the gas recycle arrangement may include a gas separation arrangement, known in the art. The gas separation arrangement may be operable to separate the mixture of gases into individual gases that are subsequently transmitted to the second inlet of the second reactor. In an example, the gas recycle arrangement removes any impurities that may be present in the excess gases.

Optionally, the system further comprises a carbon dioxide extractor to extract carbon dioxide from atmosphere, wherein the carbon dioxide extractor is connected to the second reactor via an inlet. The carbon dioxide extractor is typically a means for absorbing carbon dioxide, such as direct air capture. Optionally, the carbon dioxide extractors are sorbent materials that absorb carbon dioxide in its gaseous form, compressed and sequestered (such as in the form of carbonate salts). The collected (absorbed or extracted) carbon dioxide is provided to the second reactor for growing microbial mass therein.

Optionally, the system further comprises a third reactor to collect and treat urea from the organism, wherein the third reactor is connected to the second reactor for providing the treated urea to the second reactor as an additional growth media component for the growth of microbial mass.

Optionally, the system is a closed-cycle system. The term "closed-cycle system" as used herein refers to a closed-loop bioregenerative life support system for occupants, such as humans and animals accompanying human. Notably, the closed-cycle system is configured and operable to achieve complete self-sufficiency in air, water and nutrients recycling. In this regard, the closed-cycle system utilizes bio-waste, for example human excreta, for growing microbial mass responsible for nutrient recycling. Optionally, the closed-cycle system may be equipped with recycling animals, edible animals, plant systems for providing additional support to the functioning of said system. For example, the closed-cycle system may be a space shuttle on long-term missions, a disaster management capsule, a war-safety tunnel, an extreme-climate abode, a continuous bioreactor tank, and so forth.

Optionally, the system is configured for use in one or more environment conditions ranging between gravitational field and non-gravitational field. It will be appreciated that the system of the present disclosure is configures with controller arrangements for controlling the first set of operative parameters and the second set of operative parameters in the first reactor and the second reactor, respectively. Therefore, the said system may be configured for adjusting (from within the system or by external controlling systems) the first set of operative parameters and the second set of operative parameters in the first reactor and the second reactor, respectively, for suitable operation of the said system in any atmospheric conditions, namely, gravity, negative gravity, partial gravity (such as low gravity or microgravity), and no gravity at all. Optionally, the system comprises a gravity sensor.

Optionally, the second reactor comprises a rotator to generate centrifugal effect to the growth media when in use in non-gravitational field conditions. Optionally, the rotator may be functionally and structurally similar to the stirrer of the second reactor. The rotator may be at least one in number and may be arranged on the walls of the second reactor to enable mixing of the growth media under the effect of negative-, partial- or non-gravitational field conditions. It will be appreciated that in partial- or non-gravitational conditions that growth media will not be at the bottom of the second reactor, and thus the stirrer may not be sufficient in mixing the growth media. In such case, rotator(s) on the wall of the second reactor in addition to the stirrer of the second container enable efficient and effective mixing of the growth media for growing microbial mass. Optionally, the speed of the rotator may be similar to the speed of the stirrer. Alternatively, the rotator may not be functionally and structurally similar to the stirrer of the second reactor. Indeed said generating of artificial gravity for the reactor chamber allows to control growth of the microbial mass. Without artificial gravity effect (caused by centrifugal force) it would not be feasible for example add gasses and nutrients to the growth media.

Optionally, the second reactor comprises a set of blades to form droplets of the growth media when in use in non-gravitational field conditions. Optionally, the set of blades may be arranged with the stirrer and/or rotator. Alternatively, optionally, the set of blades may be arranged on walls of the second reactor. It will be appreciated that water forms spherical droplets in non-gravitational field conditions. Therefore, the liquid phase of the growth media forms droplets when mixed using stirrer, rotator and/or set of blades. Optionally, the separation of liquid phase of the growth media as droplets enables flocculation of the grown microbial mass to be harvested from the outlet of the second reactor. Furthermore without the set of blades the growth media could form a single spherical liquid object inside the second reactor. This would make it difficult to control administration of $CO_2$ for example to the growth media. Small droplets can be made to move around the second reactor chamber thus enabling to provide $CO_2$ to those droplets which are in proximity of gas inlets of the reactor chamber.

The present disclosure also relates to the process as described above. Various embodiments and variants disclosed above apply mutatis mutandis to the process.

The process for growing microbial mass in non-gravitational field conditions, wherein said process comprising culturing at least one isolated microbe, comprising culturing said at least one isolated microbe in continuous culture with hydrogen as energy source and carbon dioxide as the inorganic carbon source. As mentioned before, the system is a closed-cycle system, therefore an inoculum of microbial mass comprising at least one isolated microbe, having ability to utilize hydrogen as energy source and carbon dioxide as the inorganic carbon source, is introduced and continuously cultured in the system. Notably, the said process is operable to provide desired results in both gravitational as well as non-gravitational field conditions. The isolated microbe is continuously cultured under optimum second set of operative parameters in the second reactor of the system for growing microbial mass of the said isolated microbe.

Optionally, the at least one isolated microbe is a bacterial strain of the genus *Xanthobacter*.

Optionally, the isolated bacterial strain is a VTT-E-193585 or a derivative thereof, and wherein said derivative has retained the ability to grow using hydrogen gas as energy source and carbon dioxide as the only carbon source.

Furthermore when operating in non-gravitational field conditions the treated bio-waste is provided to the second reactor from the first reactor using pressure applied to the first reactor.

In an implementation, the method and system of the present disclosure may be used to grow any type of cells, ranging from plants, animals or humans.

DETAILED DESCRIPTION OF THE DRAWINGS

Referring to FIG. 1, there is shown a flowchart 100 illustrating steps of a method for growing microbial mass, in accordance with an embodiment of the present disclosure. At step 102, biowaste is collected from an organism, the biowaste comprises a first amount of water and a first amount of solid-phase. At step 104, the collected biowaste is received in a first reactor. At step 106, the collected biowaste is treated in the first reactor using a first set of operating parameters for a first period of time to dissolve at least a part of solid-phase inorganic nutrients into the first amount of water to form a growth media. At step 107, the formed growth media is washed, wherein the washing includes sterilization, separation and cleaning steps. At step 108, the formed growth media is provided to a second reactor comprising an inoculum of microbial mass. At step 110, carbon dioxide is collected. At step 112, a second amount of water is collected and split into oxygen and hydrogen gas. At step 114, the collected carbon dioxide and the split oxygen and hydrogen gas is provided to the second reactor. At step 116, a microbial mass is grown in the second reactor under a second set of operating parameters. At step 118, the grown microbial mass is harvested from the second reactor to produce food for consumption by the organism.

The steps 102, 104, 106, 107, 108, 110, 112, 114, 116 and 118 are only illustrative and other alternatives can also be provided where one or more steps are added, one or more steps are removed, or one or more steps are provided in a different sequence without departing from the scope of the claims herein.

Figure 2:
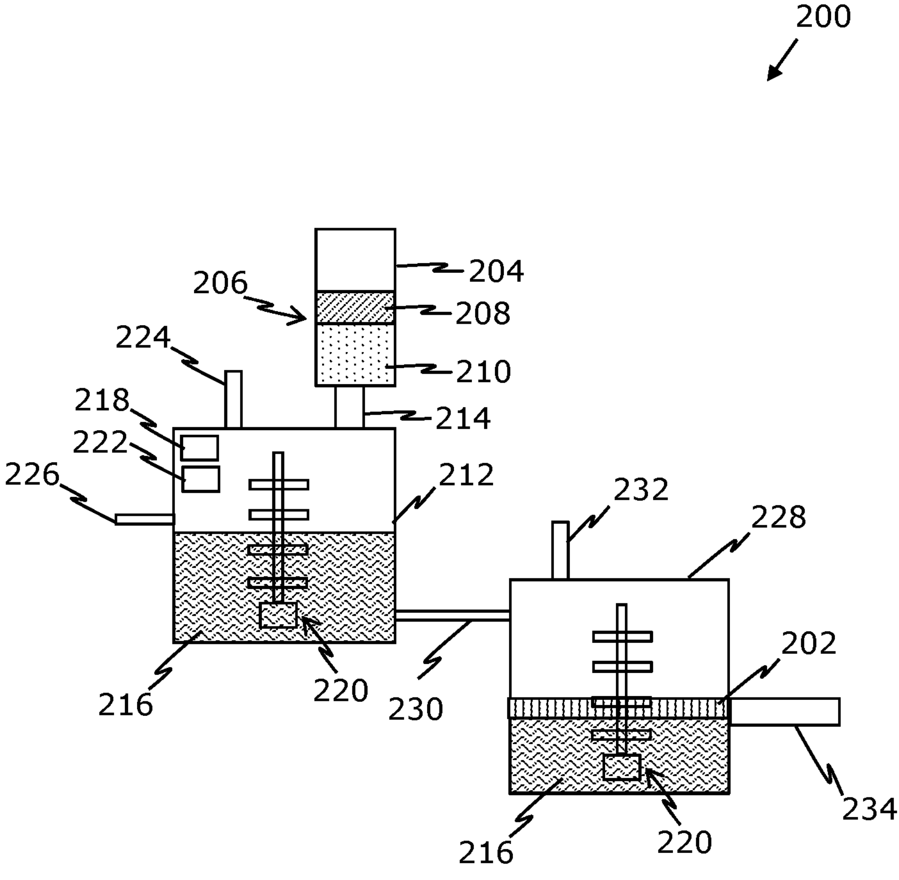
FIG. 2 is a block diagram of a system for growing microbial mass, in accordance with another embodiment of the present disclosure.

Referring to FIG. 2, there is shown a block diagram of a system 200 for growing microbial mass 202, in accordance with an embodiment of the present disclosure. The system 200 comprises a first stage 204 configured to collect biowaste 206 from an organism, the biowaste 206 comprises a first amount of water 208 and a first amount of solid-phase 210. A first reactor 212 is connected to the first stage 204 to receive the collected biowaste 206 from the first stage 204 via an inlet 214, and treat the received biowaste 206 therein to form the growth media 216.

The first reactor 206 for treating the biowaste comprises a temperature controller 218 for maintaining a desired temperature inside of the first reactor 212, a stirrer 220 for continuous mixing of the biowaste 206, a pH sensor 222, and at least one first input, such as first input 224, 226, for providing a first set of ingredients for controlling pH of the growth media 216 in the first reactor 212.

A second reactor 228 is arranged downstream from the first reactor 212, to receive the growth media 216 from the first reactor 212, via a first outlet 230, for growing microbial mass 202. The second reactor 228 comprises an inoculum of microbial mass 202, a second inlet 232 for receiving a second set of ingredients for growing microbial mass 202, the second set of ingredients comprises gases, water, and chemicals, and an outlet 234 for harvesting the grown microbial mass 202 from the second reactor 228.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method of growing a microbial mass, the method comprising a) collecting biowaste from an organism, the biowaste comprising a first amount of water and a first amount of solid-phase;

b) receiving the collected biowaste in a first reactor;

c) treating the collected biowaste in the first reactor using a first set of operating parameters for a first period of time to dissolve at least a part of solid-phase inorganic nutrients into the first amount of water to form a growth media;

d) washing the formed growth media, wherein said washing includes sterilization, separation and cleaning steps;

e) providing the formed growth media to a second reactor comprising an inoculum of microbial mass;

f) collecting carbon dioxide locally from an atmosphere;

g) collecting a second amount of water present in the atmosphere and splitting the collected second amount of water into oxygen and hydrogen gas;

h) providing the collected carbon dioxide and the split oxygen and hydrogen gas to the second reactor;

i) growing a microbial mass in the second reactor under a second set of operating parameters; and j) harvesting the grown microbial mass from the second reactor to produce food for consumption by the organism.

2. The method according to claim 1, wherein the amount of water in the growth media is adjusted by adding a third amount of water to the first reactor if the amount of water in the growth media is less than 20 weight percent of the growth media, and adding more solid-phase if the amount of water in the growth media is more than 20 weight percent of the growth media.

3. The method according to claim 1, wherein the first set of operating parameters comprises of a temperature inside of the first reactor, wherein the temperature is at least 190 degrees Celsius; and a pH of the growth media, wherein the pH is less than 4.

4. The method according to claim 1, wherein the method further comprises stirring the biowaste in the first reactor at a speed of at least 100 RPM.

5. The method according to claim 1, wherein the first period of time is one hour to 18 hours.

6. The method according to claim 1, wherein biowaste comprises feces and urine and the first amount of water is 50-90 weight percent of the biowaste.

7. The method according to claim 1, wherein the method further comprises extracting carbon dioxide from at least a part of the growth media.

8. The method according to claim 1, wherein the inoculum of microbial biomass comprises at least one isolated microbe, wherein said microbe has ability to grow using hydrogen gas as energy source and carbon dioxide as an inorganic carbon source.

9. The method according to claim 8, wherein the microbes for the inoculum are selected from a group of: *Clostridium ljungdahlii, Saccharomyces cerevisiae*, Knallgas bacteria, genus *Caminibacter*, genus *Aquifex*, genus *Paracoccus*, genus *Xanthobacter*, genus *Hydrogenomonas, methanotrophs, methanogens*, genus *Geobacter*, genus *Cyanobacterium*, genus *Acetobacterium*, genus *Oscillospira*, genus *Pleomorphomonas*.

10. The method according to claim 1, wherein the growing of the microbial mass comprises culturing a bacterial strain of the genus *Xanthobacter* in continuous culture with hydrogen as energy source and an inorganic carbon source, wherein the inorganic carbon source comprises carbon dioxide.

11. The method according to claim 1, wherein the microbial mass comprises an isolated bacterial strain VTT-E-193585 or a derivative of VTT-E-193585 which has retained the ability to grow using hydrogen gas as energy source and carbon dioxide as the only carbon source.

12. The method according to claim 1, wherein the method further comprises collecting urea from the organism, providing the collected urea to a third reactor for a treatment thereof and providing the treated urea from the third reactor to the second reactor as an additional growth media component for the growth of microbial mass.

13. The method according to claim 1, wherein the microbial mass is operable to recycle the biowaste and gases into food for consumption by the organism, and wherein the food is rich in at least one of: a protein, a carbohydrate, a fatty acid, an antioxidant, a fibre content.

14. The method according to claim 1, wherein the growing of microbial mass occurs in non-gravitational field conditions, wherein said process comprising culturing at least one isolated microbe, comprising culturing said at least one isolated microbe in continuous culture with hydrogen as energy source and carbon dioxide as the inorganic carbon source.

15. The method according to claim 14, wherein the at least one isolated microbe is a bacterial strain of the genus *Xanthobacter*.

16. The method according to claim 14, wherein the isolated bacterial strain is a-VTT-E-193585 or a derivative of VTT-E-193585 which has retained the ability to grow using hydrogen gas as energy source and carbon dioxide as the only carbon source.

* * * * *